(12) United States Patent
Sola i Caros et al.

(10) Patent No.: US 10,058,251 B2
(45) Date of Patent: Aug. 28, 2018

(54) METHOD FOR DETERMINING NON-INVASIVELY A HEART-LUNG INTERACTION

(75) Inventors: Josep Sola i Caros, Neuchâtel (CH); Josef X. Brunner, Chur (CH)

(73) Assignee: CSEM CENTRE SUISSE D'ELECTRONIQUE ET DE MICROTECHNIQUE SA—RECHERCHE ET DÉVELOPPEMENT, Neuchatel (CH)

( * ) Notice: Subject to any disclaimer, the term of this patent is extended or adjusted under 35 U.S.C. 154(b) by 171 days.

(21) Appl. No.: 14/115,384

(22) PCT Filed: May 2, 2012

(86) PCT No.: PCT/EP2012/058022
§ 371 (c)(1),
(2), (4) Date: Dec. 18, 2013

(87) PCT Pub. No.: WO2012/150258
PCT Pub. Date: Nov. 8, 2012

(65) Prior Publication Data
US 2014/0094664 A1    Apr. 3, 2014

(30) Foreign Application Priority Data

May 2, 2011 (CH) .......................... 745/11

(51) Int. Cl.
*A61B 5/0205* (2006.01)
*A61B 5/053* (2006.01)
(Continued)

(52) U.S. Cl.
CPC ............ *A61B 5/0205* (2013.01); *A61B 5/021* (2013.01); *A61B 5/029* (2013.01);
(Continued)

(58) Field of Classification Search
CPC .............. A61B 5/0205; A61B 5/02028; A61B 5/02405; A61B 5/02416; A61B 5/0295; A61B 5/029; A61B 5/0536; A61B 5/0535
(Continued)

(56) References Cited

U.S. PATENT DOCUMENTS

2003/0167010 A1   9/2003  Pinsky et al.
2004/0249297 A1*  12/2004 Pfeiffer et al. ................ 600/526
(Continued)

OTHER PUBLICATIONS

Eyuboglu, B.M. et al, Localisation of cardiac related impedance changes in the thorax, Clin. Phys. Physiol. Meas.., 1987, vol. 8, Suppl. A, 167-173, Great Britain.
(Continued)

*Primary Examiner* — Adam J Eiseman
(74) *Attorney, Agent, or Firm* — Pearne & Gordon LLP (57) ABSTRACT

The present disclosure concerns a method for determining a heart-lung interaction factor of a subject, comprising: measuring a heart activity-related signal comprising heart activity-related information; from the heart activity-related signal, calculating a frequency of cardiac cycle and a frequency of respiratory cycle; from the heart activity-related signal, determining a cardiac cycle energy at the frequency of cardiac cycle, determining a respiratory cycle energy at the frequency of respiratory cycle, and determining a heart-lung interaction energy at an intermodulation frequency corresponding to the difference between the frequency of respiratory cycle and the frequency of cardiac cycle, or the sum of the frequency of respiratory cycle and the frequency of cardiac cycle; and determining a heart-lung interaction factor from the ratio of the heart-lung interaction energy and one of the cardiac cycle energy and the respiratory cycle energy. The heart-lung interaction factor can be determined non-invasively.

21 Claims, 2 Drawing Sheets

(51) Int. Cl.
  A61B 5/02    (2006.01)
  A61B 5/021   (2006.01)
  A61B 5/029   (2006.01)
  A61B 5/0402  (2006.01)
  A61B 5/00    (2006.01)
  A61B 7/04    (2006.01)
  A61B 8/08    (2006.01)
  A61B 5/024   (2006.01)
(52) U.S. Cl.
  CPC ........ *A61B 5/02028* (2013.01); *A61B 5/0402* (2013.01); *A61B 5/0536* (2013.01); *A61B 5/7257* (2013.01); *A61B 7/04* (2013.01); *A61B 8/08* (2013.01); *A61B 5/02416* (2013.01)
(58) Field of Classification Search
  USPC ........................................................ 600/547
  See application file for complete search history.

(56) References Cited

U.S. PATENT DOCUMENTS

| 2007/0179386 | A1* | 8/2007  | Michard et al. | 600/485 |
| 2008/0033306 | A1  | 2/2008  | Joeken         |         |
| 2008/0294060 | A1* | 11/2008 | Haro et al.    | 600/538 |
| 2010/0292584 | A1* | 11/2010 | Lee            | 600/485 |
| 2010/0324428 | A1* | 12/2010 | Pfeiffer       | 600/490 |
| 2014/0286556 | A1* | 9/2014  | Fouras et al.  | 382/131 |
| 2014/0316278 | A1* | 10/2014 | Addison et al. | 600/476 |

OTHER PUBLICATIONS

Cannesson et al., Pleth variability index to monitor the respiratory variations in the pulse oximeter plethysmographic waveform amplitude and predict fluid responsiveness in the operating theatre, British Journal of Anaesthesia 101 (2): 200-6 (2008), doi:10.1093/bja/aen133 Advance Access publication Jun. 2, 2008.

Frederic Michard and Jean-Louis Teboul, Using heart-lung interactions to assess fluid responsiveness during mechanical ventilation, Current Science Ltd (Print ISSN 1364-8535; Online ISSN 1466-609X), Sep. 1, 2000, http://ccforum.com/content/4/5/282.

International Search Report for PCT/EP2012/058022 dated Jul. 30, 2012.

* cited by examiner

Fig. 1

| Frequency component | Content |
|---|---|
| DC (constant value) | MAP |
| Heart Frequency ($f_h$) | $A_h$ |
| Respiration frequency ($f_r$) | MAP HLI |
| Intermodulation frequency ($f_r$-$f_v$) | $\frac{1}{2}$HLI $A_h$ |
| Intermodulation frequency ($f_r$-$f_v$) | $\frac{1}{2}$HLI $A_h$ |

METHOD FOR DETERMINING NON-INVASIVELY A HEART-LUNG INTERACTION

FIELD

The present disclosure concerns a method for determining non-invasively a heart-lung interaction factor. The present disclosure further concerns a method for determining non-invasively a predictor of fluid responsiveness using the heart-lung interaction factor.

BACKGROUND

Interaction between respiratory and heart activities occurs anywhere within the thoracic cavity and can be extracted reliably from signals obtained directly within central blood vessels such as the aorta.

It is known in the art that either the positive pressures applied during mechanical ventilation or the negative intra-thoracic pressures during spontaneous breathing induce cyclic changes in left ventricular stroke volumes. The more both the right and the left ventricle become preload dependent, the more likely they will respond positively to the administration of intravascular fluids. As described by Michard et al. in their review article (Michard et al. Crit Care 2000, 4:282-289) mainly the Frank-Starling relationship determines a living being's response to volume expansion. Clinical data demonstrate that respiratory-induced variations in arterial pulse pressure (PPV), in systolic pressure (SPV), but more importantly in left ventricular stroke volume (SVV), which can be determined by the surrogate parameters of Doppler aortic blood flow velocity, can be used to detect biventricular preload dependence, and hence be exploited as surrogates for fluid responsiveness in living beings, particularly in critically ill patients. Although the names of these different parameters (PPV and SVV) do not directly elude to them as being direct or indirect measures of fluid responsiveness, a newly introduced fluid responsiveness index (FRI) does this in an explicitly way (see U.S. 2008/0033306).

Despite the fact that the described parameters of heart-lung interaction are of utmost clinical importance, to date none of them can be measured non-invasively. While U.S. patent 2008/0033306 suggests more advanced and sophisticated algorithms to extract rather reliable information on heart-lung-interaction and fluid responsiveness in ventilated as well as non-ventilated patients, it remains entirely depend on signals obtained from invasive pressure measurements in central arteries such as the aorta, the femoral or brachial arteries. Thus, while the proposed approach to a more robust determination of fluid responsiveness has to be applauded, it does not address the underlying problem of invasiveness.

A first non-invasive approach to assess heart-lung interactions via a non-invasive technique is that proposed by Masimo (Irvine, US) based on the analysis of photo-plethysmographic time series at peripheral measurement sites such as the finger tip. Masimo introduced the so-called Pleth Variability Index (PVI) (Cannesson et al, British Journal of Anesthesia 2008; 101: 200-206). Unfortunately, PVI relies on the analysis of pulsatility signals from very distal arteries of the muscular type. The characteristics of these arteries, however, are substantially different from those of central arteries such as the aorta. Thus, by nature of the approach PVI can provide nothing else but non-central estimates of heart-lung interaction: local vasoconstriction phenomena are prone to bias such estimates, especially in hemodynamically critical situations in which the information on fluid responsiveness is needed the most. Thus, while the proposed approach addresses the non-invasiveness, the fact that it relies on distal photo-plethysmographic signals constraints its application: it does not provide a method for analyzing central hemodynamics.

Control of cardiovascular instability is crucial when treating critically ill patients. Clinical assessment and treatment of intravascular fluid status are usually guided by arterial filling pressures. However, the clinical value of these pressure-related filling parameters in states of critical illness and during positive pressure ventilation has been questioned repeatedly and fundamentally: central venous and pulmonary artery occlusion pressures poorly predict the hemodynamic response to a fluid challenge. Pressure-based concepts are inferior to volume-based concepts as they are substantially influenced by intra-thoracic pressures. Thus, they do not allow inferences on cardiac preload. Functional hemodynamic parameters derived from invasive arterial pressure or flow signals, quantifying the interactions between heart and lungs, known as heart-lung interaction (HLI), pulse pressure variations (PPV), left ventricular stroke volume variations (SVV) or systolic pressure variations (SPV) have shown to be clinically superior. However, current methods for determining such parameters are usually performed in the time domain rendering them susceptible to artifacts and noise. Thus, more robust means of calculating these parameters are highly desirable.

Furthermore, the above mentioned parameters can be calculated reliably only from signals which need to be obtained by invasive catheters, with their associated risks and complications. Therefore, not only more robust but also less invasive means of obtaining reliable predictors of fluid responsiveness or heart-lung interaction are needed.

EIT is a non-invasive functional imaging technology that measures changes in bio-impedance at skin electrodes to reconstruct sequences of cross-sectional functional images. The methodology of EIT can be used for monitoring a patient's responsiveness to intravascular volume loading as the changes in bio-impedance are directly related to changes in stroke volumes, which result from changes in cardiac preload whereas pressure-based parameters such as PPV or SPV reflect only the results of such volume changes but not their underlying cause. However, in EIT more than 90% of the signal amplitude at the thoracic surface is due to breathing. Therefore, it becomes challenging to exploit the small ventilation-modulated variations in stroke volume, which account for no more than 1 to 2% of the total signal strength. Conventional EIT post-processing techniques are unable to analyze such low-amplitude events.

To date, assessing SVV in living beings, particularly in critically ill patients with adequate accuracy can only be achieved by obtaining blood flow or pressure signals within the most central arteries. Attempts of using signals from less invasive peripheral arteries, or even from noninvasive pulse oximetry showed promising results under stable hemodynamic conditions, but unfortunately failed during cardiovascular instability. The reasons are obvious: whenever the hemodynamic status becomes unstable, the vascular tone of peripheral arteries is adapted either as a result of endogenous counter-regulation or of treatment by vasoactive medication. Additionally, reduced peripheral perfusion, as in shock further reduces signal quality, thereby limiting even more the usefulness of the less invasive approaches currently en vogue.

It is an aim of the present invention to obviate, or mitigate, at least some of the above-mentioned disadvantages.

SUMMARY

According to the present invention, there is provided a method for determining heart-lung interaction phenomena of a living being, comprising: at least one physiological signal representing heart activity-related information; processing means for calculating frequency values of heart ($f_h$) and respiratory ($f_r$) activities contained within said signal; processing means for calculating frequency values of heart-lung interaction ($f_{hli}$) contained within said signal; processing means for calculating energy of said signal at the heart ($E_h$), respiratory ($E_r$) and heart-lung interaction ($E_{hli}$) frequencies; processing means for combining said $E_{hli}$ energy value and at least one of $E_r$ and $E_h$ energy values within one combined variable; processing means for transforming said combined variable into an index representing heart-lung interaction phenomena.

Advantageously the method and apparatus of the present invention enable assessment of heart-lung interactions in the cardiovascular system of living beings, by analyzing signals from central arteries, in a non-invasive manner. None of the methods known in the state of the art are capable of addressing these three requirements simultaneously.

The present invention enables the determination of SVV in the descending aorta by analyzing sequences of EIT images in the frequency-domain ($SVV_{EIT}$).

Heart-lung interaction (HLI) describes the amount of interaction between respiratory activity and left ventricular function: by instance, a HLI index might quantify the amount the different ejected left ventricular volumes during inspiration and expiration. Heart-lung interactions (HLI) include, but are not limited to, pulse pressure variations (PPV), left ventricular stroke volume variations (SVV) and/or systolic pressure variations (SPV).

The physiological signal representing heart activity-related information may be an arterial pressure signal.

The physiological signal representing heart activity-related information may be a photo-plethysmographic signal.

The physiological signal representing heart activity-related information may be a blood flow signal.

The physiological signal representing heart activity-related information may be a signal obtained by Electrical Impedance Tomography (EIT) means.

The signal obtained by Electrical Impedance Tomography (EIT) means may correspond to the heart activity-related impedance change time series from at least one pixel of the tomographic images.

The impedance change time series from at least one pixel of the tomographic images may correspond to functional structures of interest such as the heart.

The impedance change time series from at least one pixel of the tomographic images may correspond to functional structures of interest such as the left ventricle.

The impedance change time series from at least one pixel of the tomographic images may correspond to functional structures of interest such as the right ventricle.

The impedance change time series from at least one pixel of the tomographic images may correspond to functional structures of interest such as major arteries.

The impedance change time series from at least one pixel of the tomographic images may correspond to functional structures of interest such as the aorta.

The impedance change time series from at least one pixel of the tomographic images may correspond to functional structures of interest such as the pulmonary artery.

The processing means for calculating frequency values may be based on a Fourier periodogram technique.

The processing means for calculating frequency values may be based on a parametric periodogram technique.

The processing means for calculating frequency values may be based on the projection of said signal on trigonometric base functions.

A heart activity frequency value ($f_h$) may calculated as the frequency depicting the maximum power density in the calculated periodogram, and the respiratory activity frequency value ($f_r$) may be calculated as the frequency depicting a maximum power density at frequencies lower than $f_h$.

A respiratory activity frequency value ($f_r$) may be calculated as the frequency depicting the maximum power density in the calculated periodogram, and the heart activity frequency value ($f_h$) may be calculated as the frequency depicting a maximum power density in frequencies higher than $f_r$, excluding respiratory harmonic frequencies.

The frequency values of heart-lung interaction may be calculated from said $f_h$ and $f_r$.

A frequency value of heart-lung interaction may be calculated as $f_h - f_r$.

A frequency value of heart-lung interaction may be calculated as $f_h + f_r$.

The energy values of said heart ($E_h$), respiratory ($E_r$) and heart-lung interaction ($E_{hli}$) frequencies may be calculated from a Fourier periodogram.

The energy values of said heart ($E_h$), respiratory ($E_r$) and heart-lung interaction ($E_{hli}$) frequencies may be calculated from a parametric periodogram.

The energy values of said heart ($E_h$), respiratory ($E_r$) and heart-lung interaction ($E_{hli}$) frequencies may be calculated from a projection onto trigonometric base functions.

The energy values $E_{hli}$ and $E_h$ may be combined in a single variable as the ratio of $E_{hli}$ over $E_h$.

The energy values $E_{hli}$, $E_h$ and $E_r$ may be combined in a single variable as the ratio of $E_{hli}$ over $E_h$ and $E_r$.

The combined variable may be transformed into an index representing heart-lung interaction phenomena using a formula derived from a mathematical model.

The combined variable may be transformed into an index representing heart-lung interaction phenomena using a function obtained from a training set of data.

The value representing heart-lung interaction phenomena may be a Stroke Volume Variation (SVV) value.

The value representing heart-lung interaction phenomena may be a Pulse Pressure Variation (PPV) value.

The value representing heart-lung interaction phenomena may be a Systolic Pressure Variation (SPV) value.

The value representing heart-lung interaction phenomena may be a Plethysmographic Variability Index (PVI) value.

The value representing heart-lung interaction phenomena may be a Fluid Responsiveness Index (FRI) value.

At least one additional signal may be used to calculate frequency values of any of the heart ($f_h$) and respiratory ($f_r$) activities.

At least one additional signal may be used to calculate energy of any of the heart ($E_h$) and respiratory ($E_r$) activities.

The additional signal may be provided by independent sources such as an electrocardiogram, a phono-cardiogram, an ultrasound, a blood flow signal, a respiratory inductive or a photo-plethysmogram.

The additional signal may be provided by pixels of the Electrical Impedance Tomography images corresponding to functional structures such as the heart and the lungs.

According to a further aspect of the present invention there is provided an apparatus for determining heart-lung interaction phenomena of a living being, comprising: measuring means for obtaining at least one physiological signal representing heart activity-related information; processing means for calculating frequency values of heart ($f_h$) and respiratory ($f_r$) activities contained within said signal; processing means for calculating frequency values of heart-lung interaction ($f_{hli}$) contained within said signal; processing means for calculating energy of said signal at the heart ($E_h$), respiratory ($E_r$) and heart-lung interaction ($E_{hli}$) frequencies; processing means for combining said $E_{hli}$ energy value and at least one of $E_r$ and $E_h$ energy values within one combined variable; processing means for transforming said combined variable into an index representing heart-lung interaction phenomena.

The means for obtaining may be one physiological signal representing heart activity-related information measures an arterial pressure signal.

The means for obtaining at least one physiological signal representing heart activity-related information may be configured to measure a photo-plethysmographic signal.

The means for obtaining at least one physiological signal representing heart activity-related information may be configured to measure a blood flow signal.

The mean for obtaining at least one physiological signal representing heart activity-related information may be configured to measure a signal obtained by Electrical Impedance Tomography (EIT) means.

The signal obtained by Electrical Impedance Tomography (EIT) means may correspond to the heart activity-related impedance change time series from at least one pixel of the tomographic images.

The impedance change time series from at least one pixel of the tomographic images may correspond to functional structures of interest such as the heart.

The impedance change time series from at least one pixel of the tomographic images may correspond to functional structures of interest such as the left ventricle.

The impedance change time series from at least one pixel of the tomographic images may correspond to functional structures of interest such as the right ventricle.

The impedance change time series from at least one pixel of the tomographic images may correspond to functional structures of interest such as major arteries.

The impedance change time series from at least one pixel of the tomographic images may correspond to functional structures of interest such as the aorta.

The impedance change time series from at least one pixel of the tomographic images may correspond to functional structures of interest such as the pulmonary artery.

The processing means for calculating frequency values may be based on a Fourier periodogram technique.

The processing means for calculating frequency values may be based on a parametric periodogram technique.

The processing means for calculating frequency values may be based on the projection of said signal on trigonometric base functions.

A heart activity frequency value ($f_h$) may be calculated as the frequency depicting the maximum power density in the calculated periodogram, and the respiratory activity frequency value ($f_r$) may be calculated as the frequency depicting a maximum power density at frequencies lower than $f_h$.

A respiratory activity frequency value ($f_r$) may be calculated as the frequency depicting the maximum power density in the calculated periodogram, and the heart activity frequency value ($f_h$) may be calculated as the frequency depicting a maximum power density in frequencies higher than $f_r$, excluding respiratory harmonic frequencies.

Frequency values of heart-lung interaction may be calculated from said $f_h$ and $f_r$.

A frequency value of heart-lung interaction may be calculated as $f_h - f_r$.

A frequency value of heart-lung interaction may be calculated as $f_h + f_r$.

The energy values of said heart ($E_h$), respiratory ($E_r$) and heart-lung interaction ($E_{hli}$) frequencies may be calculated from a Fourier periodogram.

The energy values of said heart ($E_h$), respiratory ($E_r$) and heart-lung interaction ($E_{hli}$) frequencies may be calculated from a parametric periodogram.

The energy values of said heart ($E_h$), respiratory ($E_r$) and heart-lung interaction ($E_{hli}$) frequencies may be calculated from a projection onto trigonometric base functions.

The energy values $E_{hli}$ and $E_h$ may be combined in a single variable as the ratio of $E_{hli}$ over $E_h$.

The energy values $E_{hli}$, $E_h$ and $E_r$ may be combined in a single variable as the ratio of $E_{hli}$ over $E_h$ and $E_r$.

The combined variable may be transformed into an index representing heart-lung interaction phenomena using a formula derived from a mathematical model.

The combined variable may be transformed into an index representing heart-lung interaction phenomena using a function obtained from a training set of data.

The value representing heart-lung interaction phenomena may be a Stroke Volume Variation (SVV) value.

The value representing heart-lung interaction phenomena may be a Pulse Pressure Variation (PPV) value.

The value representing heart-lung interaction phenomena may be a Systolic Pressure Variation (SPV) value.

The value representing heart-lung interaction phenomena may be a Plethysmographic Variability Index (PVI) value.

The value representing heart-lung interaction phenomena may be a Fluid Responsiveness Index (FRI) value.

At least one additional signal may be used to calculate frequency values of any of the heart ($f_h$) and respiratory ($f_r$) activities.

At least one additional signal may be used to calculate energy of any of the heart ($E_h$) and respiratory ($E_r$) activities.

The additional signal may be provided by independent sources such as an electrocardiogram, a phono-cardiogram, an ultrasound, a blood flow signal, a respiratory inductive or a photo-plethysmogram.

The additional signal may be provided by pixels of the Electrical Impedance Tomography images corresponding to functional structures such as the heart and the lungs.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS

Heart-related activity in arteries of a subject (living being human or animal) as a function of time t can be modeled mathematically by equation 1:

$$\text{heart}(t) = \text{MAP} + A_h \sin(2\pi f_h t) \quad \text{(Equation 1)}$$

wherein MAP is Mean Arterial Pressure, $A_h$ is the amplitude of a heart activity-related signal, $f_h$ is the frequency of the heart cycle (cardiac frequency or cardiac cycle). Here, the expressions heart-related activity and heart activity-related signal should be interpreted as including cardiac-related activity and cardiac related signal. In an embodiment, the heart activity (or cardiac)-related signal comprises an arterial pressure signal.

The heart activity-related signal can also comprise a photoplethysmographic signal, a blood flow signal, or any other suitable signal.

Similarly, the respiratory activity of the subject as a function of time t can be modeled by equation 2:

$$\text{resp}(t) = \sin(2\pi f_r t) \quad \text{(Equation 2)}$$

wherein $f_r$ is the frequency of the respiratory cycle (breathing cycle) of the subject.

A heart-lung interaction can be modeled by a multiplicative model, as depicted as Equation 3:

$$hli(t) = \text{HLI heart}(t)\text{resp}(t) \quad \text{(Equation 3)}$$

wherein HLI is a Heart-Lung Interaction factor, the target index of the current invention. The HLI value contains information on the quantity of such interaction between the respiratory activity of the subject and circulation and is directly related to fluid responsiveness parameters such as Stroke Volume Variations (SVV), Pressure Pulse Variations (PPV) and the likes.

Equation 3 can be developed as:

$$hli(t) = \text{HLI}[\text{MAP} + A_h \sin(2\pi f_h t)]\sin(2\pi f_r t) \quad \text{(Equation 4)}$$

Developing this equation further one obtains:

$$\frac{1}{2}\text{MAP } A_h[\sin(2\pi(f_h - f_h)t) + \sin(2\pi(f_h + f_h)t)] \quad \text{(Equation 5)}$$

A circulatory-related signal can be described by Equations 6 and Equation 7:

$$\text{circ}(t) = \text{heart}(t) + hli(t) \quad \text{(Equation 6)}$$

$$\frac{1}{2}\text{HLI } A_h[\sin(2\pi(f_h - f_h)t) + \sin(2\pi(f_h + f_h)t)] \quad \text{(Equation 7)}$$

Figure 1:
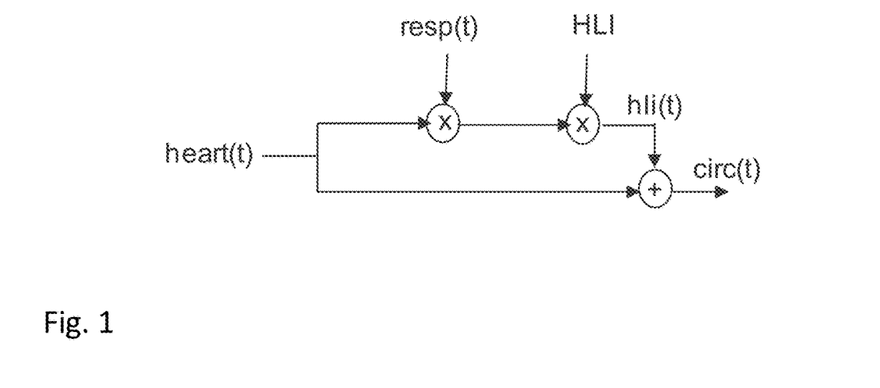
FIG. 1 shows an equivalent model of a circulatory-related signal, according to an embodiment.
Figure 2:
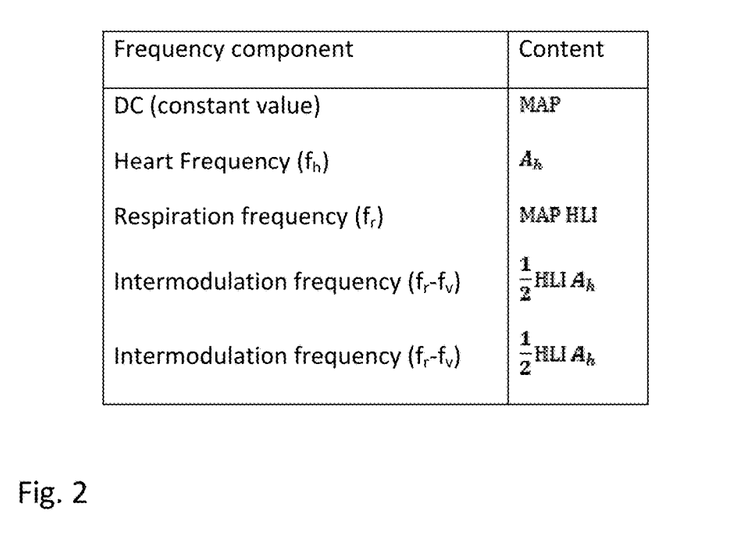
FIG. 2 shows a table summarizing frequency components calculated from a circulatory-related signal, according to an embodiment.

The calculated circulatory-related signal corresponds to a physiological signal that would be measured using a physiological sensor indicative of blood volume, An equivalent model of the circulatory-related signal is shown in FIG. 1. FIG. 2 is a table summarizing the frequency components that a circulatory-related signal according to the model described in Equation 7 would depict. As mentioned above, MAP is Mean Arterial Pressure, $A_h$ is the amplitude of the heart activity-related signal and HLI is the Heart-Lung Interaction factor.

Note that the model of the circulatory-related signal represented in FIG. 1, is similar to an Amplitude Modulation model (AM), as known by a person skilled in the art of electronic communications. In particular, by assuming that the circulatory-related signal is generated by:

$$\text{circ}(t) = [\text{MAP} + A_h\sin(2\pi f_h t)][1 + \text{HLI}\sin(2\pi f_r t)] \quad \text{(Equation 8)}$$

one obtains the same development as in Equation 7, and the same frequency components as in Table 1. A person skilled in the art will further interpret Equation 8 as follows: respiratory activity modulates the heart-related activity of a living cardiovascular system via an amplitude modulation process with a modulation factor of HLI.

According to an embodiment, a method for determining the heart lung interaction factor comprises the steps of:
- measuring the heart activity-related signal comprising heart activity-related information;
- from the heart activity-related signal, calculating the frequency of cardiac cycle $f_h$ and frequency of respiratory cycle $f_r$; and
- from the heart activity-related signal, determining a cardiac cycle energy $E_h$ at the frequency of cardiac cycle $f_h$, a respiratory cycle energy $E_r$ at the frequency of respiratory cycle $f_r$, and a heart-lung interaction energy $E_{hli}$ at an intermodulation frequency $f_{hli}$ corresponding to the difference between the frequency of respiratory cycle $f_r$ and the frequency of cardiac cycle $f_h$ ($f_{hli} = f_r - f_h$). The method further comprises dividing the calculated heart-lung interaction energy $E_{hli}$ by the cardiac cycle energy $E_h$ to obtain a ratio that depends only on HLI:

$$\frac{E_{hli}}{E_h} = \frac{\frac{1}{2}HLI A_h}{A_h} = \frac{1}{2}HLI \quad \text{(Equation 9)}$$

Therefore, the heart-lung interaction factor HLI can be obtained from the ratio of the heart-lung interaction energy $E_{hli}$ over the cardiac cycle energy $E_h$.

Alternatively, the heart-lung interaction factor HLI can be obtained from the ratio of the heart-lung interaction energy $E_{hli}$ over the respiratory cycle energy $E_r$. The intermodulation frequency $f_{hli}$ can be calculated from the frequency of cardiac cycle $f_h$ and the frequency of respiratory cycle $f_r$. For example, the intermodulation frequency $f_{hli}$ can be calculated as $f_h - f_r$ (HLI−) or as $f_h + f_r$ (HLI+).

Since none of the values required to calculate the HLI index as depicted in Equation 10 are dependent on mean arterial pressure (MAP), the method of the present invention is suitable for use under those conditions where only a signal proportional to arterial pulse pressure is available. This unique feature allows HLI to be estimated from non-invasive surrogates of arterial pressure tracings such as photoplethysmography (PPG), EIT signals (see below) or ultrasound-based blood flow Doppler signals.

In an embodiment, the heart activity-related signal comprises an EIT signal obtained by using an EIT imaging measurement technique. An EIT imaging technique can comprise acquiring a temporal sequence of EIT images. Each EIT image of the sequence of EIT images comprises a plurality of pixels, each pixel representing an impedance value. From the temporal sequence of EIT images, a temporal variation of the impedance value for each pixel can be determined, such as to generate a time series for each pixel (the EIT signal). A pressure pulse corresponds to a blood bursts through vascularized structures, or arterial tree of the subject during each cardiac cycle. Assuming that the onset of the pressure pulse at a given anatomical location of the subject corresponds to the onset of an impedance pulse, Pulse Arrival Time (PAT) values can be estimated from the generates time series. Time series (or EIT signal) can be generated for a subset of the plurality pixels located in an anatomical region of interest (ROI) of the subject. For example, such a ROI can comprise the left- and/or right-ventricles of the subject, the descending aorta, the pulmonary artery, or any major arteries.

The heart-lung interaction energy $E_{hli}$ and the cardiac cycle energy $E_h$ are calculated from a time series generated from EIT signals obtained for a ROI corresponding to the descending aorta. A frequency analysis on the time series can be performed such as to estimate a spectral density of the time series. FIG. 2 depicts a Fourier periodogram of the time series of one (a single) EIT pixel containing heart activity-related pulsatility information of the descending aorta. After detecting the position of those pixels containing the desired functional information of the aorta, i.e., after detecting the ROI corresponding to the descending aorta, its time series, i.e., the time series generated for the subset of pixels comprised in said ROI, is analyzed using a Fourier periodogram.

Figure 3:
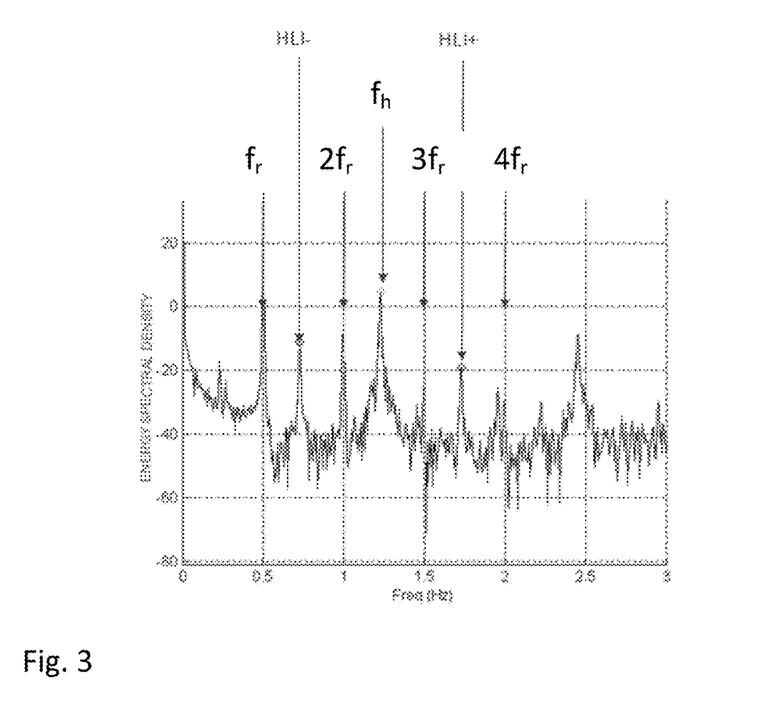
FIG. 3 illustrates a spectral density of a time series generated from EIT signals.

Referring to FIG. 3, the spectral density of the time series comprises several important energy peaks. The most relevant energy peaks are situated at the frequency of respiratory cycle $f_r$ and frequency of cardiac cycle $f_h$, as well as at the intermodulation frequency $f_{hli}$ calculated as $f_h$-$f_r$ (represented by HLI– in FIG. 3) or calculated as $f_h$+$f_r$ (represented by HLI+ in FIG. 3). The frequency of cardiac cycle $f_h$ can be determined as the frequency at the maximum power density in the periodogram (FIG. 3). More particularly, the frequency of cardiac cycle $f_h$ can be determined as the frequency at the maximum power density in the calculated periodogram, and the frequency of respiratory cycle $f_r$ can be determined as the frequency at the maximum power density at frequencies being lower than $f_h$. Alternatively, the frequency of respiratory cycle $f_r$ can be determined as the frequency at the maximum power density in the periodogram, and the frequency of cardiac cycle $f_h$ can be determined as the frequency at a maximum power density at frequencies higher than $f_r$, excluding respiratory harmonic frequencies. In addition, several harmonics of the respiratory energy peak are located at the frequencies $2f_r$, $3f_r$ and $4f_r$ in FIG. 3.

According to Equation 10, an estimation of the heart-lung interaction factor HLI is obtained by dividing the heart-lung interaction energy $E_{hli}$ calculated at the peak at the HLI– (or HLI+) frequency over the cardiac cycle energy $E_h$ calculated at frequency $f_h$, as provided by the periodogram.

Instead of a Fourier periodogram several other periodograms techniques could alternatively be used, such as a Barlett periodogram, a parametric periodogram (by instance an AR-based periodogram, Proakis and Manolakis, Prentice Hall, 1995) or a periodogram based on on the projection on trigonometric base functions (Vetter et al., Proc. World Congress Medical Physics and Biomedical Engineering 2009, 25-4: 326-329). For example, the frequency of cardiac cycle $f_h$, the frequency of respiratory cycle $f_r$ and the intermodulation frequency $f_{hli}$ can be determined from a parametric periodogram technique, or on a projection of the signal on trigonometric base functions.

In another embodiment, at least one additional signal is used to determine the frequency of cardiac cycle $f_h$ and the frequency of respiratory cycle $f_r$. The additional signal can also be used to calculate the cardiac cycle energy $E_h$ and the respiratory cycle energy $E_r$. The additional signal can be provided by independent measurement sources such as an electrocardiogram, a phono-cardiogram, an ultrasound, a blood flow signal, a respiratory inductive or a photo-plethysmogram. The additional signal can also be provided from pixels of EIT images measured in a ROI corresponding to functional structures such as the heart and the lungs.

The cardiac cycle energy $E_h$ at the frequency of cardiac cycle $f_h$, the respiratory cycle energy $E_r$ and the heart-lung interaction energy $E_{hli}$ frequencies are calculated from the Fourier periodogram, from the a parametric periodogram technique, or from a projection onto trigonometric base functions.

For sake of completeness, estimating HLI can be compared to the Pulse Pressure Variation (PPV) method as disclosed by Michard et al. in their U.S. patent 2007/0179386. According to this method, a pulse pressure variation expressed in percentage (ΔPP) can be defined as (Equation 10):

$$\Delta PP(\%) = 100 \times \frac{(PP_{MAX} + PP_{MIN})}{(PP_{MAX} + PP_{MIN})/2} \qquad \text{Equation 10}$$

The term ($PP_{max}$–$PP_{min}$) of Equation 10 can be associated with the amplitude of a cardiovascular signal at the respiratory frequency, which corresponds to MAP HLI. Similarly, the term ($PP_{max}$+$PP_{min}$)/2 of Equation 10 can also be associated with an estimate of the absolute value of blood pressure. Therefore, Equation 10 can be rewritten as:

$$\Delta PP \sim \frac{(PP_{MAX} + PP_{MIN})}{(PP_{MAX} + PP_{MIN})/2} = \frac{MAP\ HLI}{SYS} \sim HLI \qquad \text{Equation 11}$$

Equation 11 shows that the HLI calculation is closely related to Michard's index of heart lung interaction, i.e., ΔPP.

Figure 4:
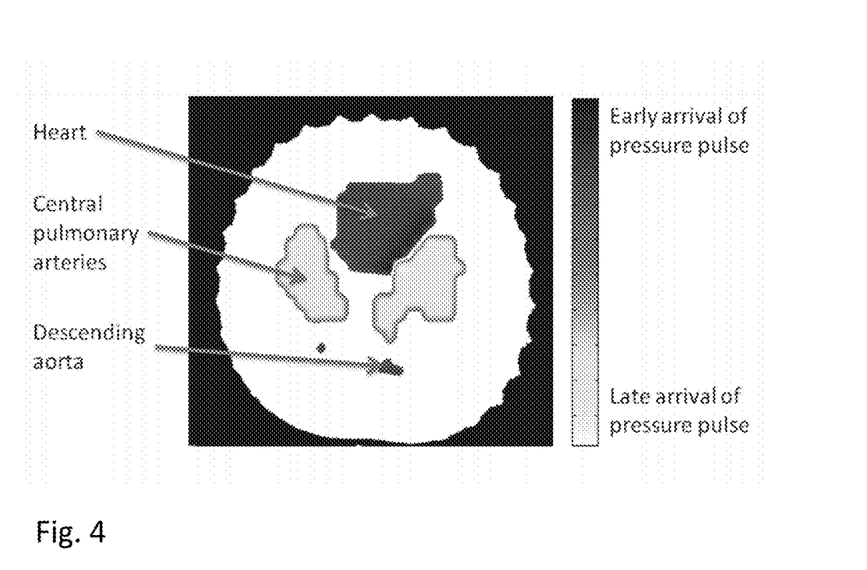
FIG. 4 represents an EIT image of a thorax showing organs and structures of interest, according to an embodiment.

Quantifying the heart-lung-interaction non-invasively by using an EIT-based method may comprise the step of identifying intra-thoracic organs and vascular structures within EIT images based on a Pulse Transit Time (PTT) analysis (i.e., identifying the ROI in EIT images). Since pressure pulses of each cardiac cycle move a burst of electrically conductive blood within the arterial tree, the corresponding EIT impedance pulses can be tracked over time. Accordingly, a new EIT image is created by assigning to each image pixel the time value at which an impedance pulse reached the underlying anatomical structure. FIG. 4 represents an EIT image of a thorax showing organs and structures of interest (ROI). Identification of the heart and main intra-thoracic vascular structures can be achieved by assignment of arrival times of arterial pressure pulses to each one of the EIT pixels representing them. Due to the high propagation velocity of pressure pulses in systemic arteries, the ROI corresponding to descending aorta is identified as those pixels located centrally behind the central pulmonary arteries for which timing values are lowest. Such identification of the ROI using the EIT imaging technique has been discussed in not yet published patent applications PCT/EP2011/061757 and PCT/EP2011/061753 by the same applicant.

Automated and unsupervised identification routines then clustered these EIT pixels in functional units based on their pulse arrival time values. EIT pixels containing information on the descending aorta are contained within a cluster located centrally behind the lungs for which PTT were lowest. In other words, the ROI corresponding to the descending aorta was determined by using automated and unsupervised identification routines.

Secondly, signals from the EIT pixels which were identified as containing information on the descending aorta (i.e. the subset of pixels comprised in the ROI corresponding to the descending aorta) are further processed to quantify their ventilation-induced modulation of cardiac impedance pulses (i.e., stroke volume variation $SVV_{EIT}$). Because of the noisy nature of EIT impedance pulses during ventilation periods a new frequency-domain technique is employed, as opposed to traditional time-based approaches.

Stroke volume variation SVV can be estimated by measuring the energy of the interaction between cardiogenic activity at the heart frequency $f_h$ and ventilation activity at respiration frequency $f_r$ for these aortic pixels. Assuming such interaction to be a modulation process, $SVV_{EIT}$ is then expressed as a function of the energy measured at the intermodulation frequency $f_h$–$f_r$. Frequency analysis is then implemented by projecting raw impedance series of aortic pixels on $f_h$, $f_r$ and $f_{h-r}$ principal frequency components.

A predictor of fluid responsiveness is computed from the heart-lung interaction factor HLI. In an embodiment, the predictor of fluid responsiveness is computed from the heart-lung interaction factor HLI by fitting the determined heart-lung interaction factor HLI with measured reference values of the predictor of fluid responsiveness. For example, the predictor of fluid responsiveness can be a stroke volume variation SVV. In particular, the stroke volume variation SVV can be computed by fitting (or calibrating) the determined heart-lung interaction factor HLI with measured reference SVV values, e.g., obtained using a standard SVV measuring device such as an ultrasound-based SVV measuring device ($SVV_{US}$) or a pulse contour-based SVV measuring device, or any other appropriate SVV measuring device ($SVV_{PC}$).

In an embodiment, the estimated energy at the intermodulation frequency is converted into SVV ($SVV_{EIT}$) values by applying a pre-trained linear transformation. In other words, values of the stroke volume variation SVV can be computed by applying a pre-trained linear transformation to the determined heart-lung interaction factor HLI. The pre-trained linear transformation is obtained from data series from a number of test subjects; in particular, these data series are used to calculate the best linear transformation between estimated HLI values and reference SVV values (in [%] units). Data series of a plurality of test subjects can also be used to analyze the correlations of $SVV_{EIT}$ with both $SVV_{US}$ and $SVV_{PC}$.

Alternatively, the heart-lung interaction factor HLI can also be used to compute a value of Pulse Pressure Variation (PPV), Systolic Pressure Variation (SPV), Plethysmographic Variability Index (PVI), or Fluid Responsiveness Index (FRI). Here, the PPV, SPV, PVI and FRI can be computed by fitting (or calibrating) the determined heart-lung interaction factor HLI with measured reference PPV, SPV, PVI and FRI values, respectively.

Accordingly, in the present invention advanced processing of EIT signals from selected pixels allows an automated, continuous and non-invasive assessment of ventilation-induced left ventricular stroke volume variation in central arteries.

The present disclosure also pertains to an apparatus for determining the predictor of fluid responsiveness of a subject from the heart-lung interaction factor (HLI), the device comprising a device for measuring a heart activity-related signal comprising heart activity-related information; a device for carry out the method disclosed herein.

REFERENCE NUMBERS $E_h$ cardiac cycle energy
$E_r$ respiratory cycle energy
$E_{hli}$ heart-lung interaction energy
$f_h$ frequency of cardiac cycle
$f_{hli}$ intermodulation frequency
$f_r$ frequency of respiratory cycle
HLI heart-lung interaction factor
MAP mean arterial pressure
PPV pressure pulse variation
SVV stroke volume variation

The invention claimed is:

1. Method for assessing intravascular fluid status of a subject by determining non-invasively a functional hemodynamic parameter from a heart-lung interaction factor (HLI) of the subject, comprising:
    measuring a heart activity-related signal comprising heart activity-related information;
    from the heart activity-related signal, calculating a frequency of cardiac cycle ($f_h$) and a frequency of respiratory cycle ($f_r$);
    from the heart activity-related signal, determining a cardiac cycle energy ($E_h$) at the frequency of cardiac cycle ($f_h$), determining a respiratory cycle energy ($E_r$) at the frequency of respiratory cycle ($f_r$);
    from the heart activity-related signal, determining a heart-lung interaction energy ($E_{hli}$) at an intermodulation frequency ($f_{hli}$) corresponding to the difference between the frequency of respiratory cycle ($f_r$) and the frequency of cardiac cycle ($f_h$), or the sum of the frequency of respiratory cycle ($f_r$) and the frequency of cardiac cycle ($f_h$);
    determining said heart-lung interaction factor (HLI) from the ratio of the heart-lung interaction energy ($E_{hli}$) and one of the cardiac cycle energy ($E_h$) and the respiratory cycle energy ($E_r$); and
    determining said functional hemodynamic parameter from the heart-lung interaction factor,
    wherein said heart activity-related signal comprises an electrical impedance tomography (EIT) signal obtained from a plurality of pixels of EIT images acquired by using an EIT imaging measurement technique.

2. Method according to claim 1, further comprising computing the predictor of fluid responsiveness from the heart-lung interaction factor (HLI).

3. Method according to claim 2, wherein the predictor of fluid responsiveness comprises a stroke volume variation (SVV).

4. Method according to claim 3, wherein said computing the predictor of fluid responsiveness comprises fitting the heart-lung interaction factor HLI with measured reference stroke volume variation (SVV) values.

5. Method according to claim 2, wherein the predictor of fluid responsiveness comprises one of a pulse pressure variation (PPV), a systolic pressure variation (SPV), a plethysmographic variability index (PVI), or a fluid responsiveness index (FRI).

6. Method according to claim 1, wherein the EIT signal is obtained from a subset of the plurality pixels located in an anatomical region of interest (ROI) of the subject comprising heart activity-related information.

7. Method according to claim 6, wherein the ROI comprises the descending aorta.

8. Method according to claim 6, further comprising generating a time series from the subset of the plurality pixels of a temporal sequence of EIT images.

9. Method according to claim 8, further comprising performing a frequency analysis on the time series such as to estimate a spectral density of the time series.

10. Method according to claim 9, wherein the frequency analysis comprises one of a Fourier analysis, a parametric analysis and a projection on trigonometric base functions, and the estimated spectral density is a periodogram.

11. Method according to claim 10, wherein said determining the frequency of cardiac cycle ($f_h$) comprises determining the frequency at the maximum power density in the periodogram, and wherein said determining the frequency of respiratory cycle ($f_r$) comprises determining the frequency at the maximum power density in the periodogram at frequencies lower than ($f_h$).

12. Method according to claim 10, wherein said determining the frequency of respiratory cycle ($f_r$) comprises determining the frequency at the maximum power density in the periodogram, and wherein said determining the frequency of cardiac cycle ($f_h$) comprises determining the frequency at a maximum power density at frequencies higher than the frequency of respiratory cycle ($f_r$), excluding respiratory harmonic frequencies.

13. Method according to claim 10, wherein said determining the heart-lung interaction energy ($E_{hli}$) comprises determining the power density from the periodogram at the intermodulation frequency ($f_{hli}$).

14. Method according to claim 10, wherein said determining the cardiac cycle energy ($E_h$) comprises determining the power density from the periodogram at the frequency of cardiac cycle ($f_h$).

15. Method according to claim 10, wherein said determining the respiratory cycle energy ($E_r$) comprises determining the power density from the periodogram at the frequency of respiratory cycle ($f_r$).

16. Method according to claim 1, further comprising measuring an additional signal comprising respiratory activity-related information.

17. Method according to claim 16, wherein said calculating a frequency of cardiac cycle ($f_h$) and a frequency of respiratory cycle ($f_r$) further comprises using said additional signal.

18. Method according to the claim 16, wherein measuring an additional signal comprises using an electrocardiogram, a phono-cardiogram, an ultrasound, a blood flow signal, a respiratory inductive or a photo-plethysmogram.

19. Method according to claim 16, wherein said additional signal comprises an electrical impedance tomography (EIT) signal obtained from a plurality of pixels of EIT images acquired by using an EIT imaging measurement technique.

20. Method according to claim 19, wherein the EIT signal is obtained from a subset of the plurality pixels located in an anatomical region of interest (ROI) of the subject comprising respiratory activity-related information.

21. The method according to claim 1, wherein the step of using a physiological sensor to measure a heart activity-related signal comprising heart activity-related information, comprises using a non-invasive physiological sensor to measure a heart activity-related signal comprising heart activity-related information.

* * * * *

UNITED STATES PATENT AND TRADEMARK OFFICE
CERTIFICATE OF CORRECTION

PATENT NO. : 10,058,251 B2
APPLICATION NO. : 14/115384
DATED : August 28, 2018
INVENTOR(S) : Solà i Caros et al.

Page 1 of 1

It is certified that error appears in the above-identified patent and that said Letters Patent is hereby corrected as shown below:

In the Specification

Column 7, Line 53: please amend the equation as follows:
$$\text{circ}(t) = \text{MAP} + A_h \sin(2\pi f_h t) + \text{MAP HLI} \sin(2\pi f_r t) + \frac{1}{2} \text{HLI } A_h [\sin(2\pi(f_h - f_r)t) + \sin(2\pi(f_h + f_r)t)] \text{ (Equation 7)}$$

Column 9, Line 43: please remove "$3f_r$," and replace with --$3f_r$,--

Signed and Sealed this
Twentieth Day of November, 2018

Andrei Iancu
*Director of the United States Patent and Trademark Office*